United States Patent [19]

Takahashi et al.

[11] Patent Number: 5,405,762
[45] Date of Patent: Apr. 11, 1995

[54] CULTURE OF ALTEROMONAS AND PROCESS OF USING THE SAME TO PRODUCE AN ANTIBACTERIAL COMPOUND

[75] Inventors: Shuji Takahashi; Hideyuki Shiozawa; Hideyuki Haruyama, all of Tokyo; Takeshi Kagasaki, Iwaki; Kentaro Kodama; Akira Ishii, both of Tsukuba, all of Japan

[73] Assignee: Sankyo Company, Limited, Tokyo, Japan

[21] Appl. No.: 184,225

[22] Filed: Jan. 19, 1994

Related U.S. Application Data

[60] Division of Ser. No. 2,085, Jan. 8, 1993, Pat. No. 5,292,892, which is a continuation of Ser. No. 876,500, Apr. 30, 1992, abandoned.

[30] Foreign Application Priority Data

May 7, 1991 [JP] Japan .................................. 3-101575

[51] Int. Cl.$^6$ .......................... C12N 1/20; C12P 17/16
[52] U.S. Cl. .................................. 435/118; 435/252.1
[58] Field of Search ...................... 435/118, 252.1, 25.1

[56] References Cited

FOREIGN PATENT DOCUMENTS

| | | |
|---|---|---|
| 3602148 | 8/1986 | Germany . |
| 54-12375 | 1/1979 | Japan . |
| 54-90179 | 7/1979 | Japan . |
| 54-103871 | 8/1979 | Japan . |
| 54-125672 | 9/1979 | Japan . |
| 1565083 | 4/1980 | United Kingdom . |
| 2173499 | 10/1986 | United Kingdom . |
| WO84/01775 | 5/1984 | WIPO . |

OTHER PUBLICATIONS

Ernst B. Chain et al, "Pseudomonic Acid. Part 1. The Structure of Pseudomonic Acid A, a Novel Antibiotic produced by Pseudomonas fluorescens", (1977), pp. 294–322, *J. Chem. Soc.* Perkin Trans. I.

J. Peter Clayton et al, "The Chemistry of Pseudomonic Acid. Part 5., Structure and Chemistry of Pseudomonic Acid C. X-Ray Crystal Structure of Ethyl Monate C", (1982), pp. 2827–2833, *J. Chem. Soc.,* Perkin Trans. I.

Peter J. O'Hanlon et al, "The Chemistry of Pseudomonic Acid. Part 6. Structure and Preparation of Pseudomonic Acid D", (1983) pp. 2655–2657, *J. Chem. Soc.* Perkin Trans. I.

D. B. Stierle et al, "Pseudomonic Acid Derivatives from a Marine Bacterium", *Abstracts of Papers,* 200(2), Part 2, 20th ACS National Meeting, American Chemical Society (1990).

LiEttlinger et al, "Stoffwechselprodukte von Actinomyceten" (1959), pp. 563–568, No. 61, *Helvetica Chimica Acta,* 42.

Walter D. Celmer et al, "The Structures of Thiolutin and Aureothricin, Antibiotics Containing a Unique Pyrrolinonodithiole Nucleus", (1955), pp. 2861–2865, Structure of Thiolutin and Aureothricin.

*Angew. Chem.,* vol. 66, (1954), 745.

Walter D. Celman et al, "Characterization of the Antibiotic Thiolutin and its Relationship with Aureothricin", (1952), pp. 6304–6305, *JACS,* 74.

Bernie V. McInerney et al, "Biologically Active Metabolites From Xenorhabdus spp., Part 1. Dithiolopyrrolone Derivatives With Antibiotic Activity", *Journal of Natural Products,* 54, 774–784 (1991).

*Primary Examiner*—Herbert J. Lilling
*Attorney, Agent, or Firm*—Frishauf, Holtz, Goodman & Woodward

[57] ABSTRACT

The present invention relates to a novel antibacterial compound obtainable from the genus Alteromonas and which shares structural similarity with the pseudomonic acids.

6 Claims, No Drawings

CULTURE OF ALTEROMONAS AND PROCESS OF USING THE SAME TO PRODUCE AN ANTIBACTERIAL COMPOUND

This is a division of application Ser. No. 08/002,085 filed Jan. 8, 1993, now U.S. Pat. No. 5,292,892, issued Mar. 8, 1994, which is a continuation of application Ser. No. 07/876,500, filed Apr. 30, 1992 (abandoned).

BACKGROUND OF THE INVENTION

The present invention relates to a new compound which we have named "Thiomarinol" and which has the formula shown hereinbelow. The invention also provides methods of preparing thiomarinol comprising fermentation using a microorganism of the genus Alteromonas, and especially a strain of the new species *Alteromonas rava*, designated SANK 73390, which is itself new and forms part of the present invention. Thiomarinol has a variety of therapeutic, especially antibacterial, effects, and, thus, the invention also provides compositions and methods of therapy or prophylaxis using this compound.

Organisms of the genus Alteromonas can be isolated from seawater, and some have been shown to produce compounds of potential therapeutic use. For example, a compound known as Viscabelin has been obtained from one species of Alteromonas, and has been shown to exhibit antitumor activity (Japanese Patent Kokai Application Number Sho 63-27484).

With respect to the structure of thiomarinol, several antibiotic substances having similar structures are known, and these may be divided into three groups.

The first group comprises the pseudomonic acids, first isolated from Pseudomonas spp. These include pseudomonic acid A [produced by *Pseudomonas fluorescens*, disclosed in J. Chem. Soc. Perkin Trans. I, 294 (1977)], pseudomonic acid B [ibid, 318 (1977)], pseudomonic acid C [ibid, 2827 (1982)] and pseudomonic acid D [ibid, 2655 (1983)]. Pseudomonic acid A is marketed under the name "Bactroban" (Beecham, registered trade mark) in the form of a 2% dermatological ointment for antibacterial use.

Other pseudomonic acid derivatives have been obtained from marine bacteria [Am. Chem. Soc. Abstr. Pap., 200 (2), (1990)], but this reference does not disclose any antibacterial activity therefor.

The second group of substances sharing a similarity of structure with the compounds of the invention comprises that group which includes the antibiotics holomycin [Helv. Chim. Acta, 42, 563 (1959)], pyrrothine [J. Am. Chem. Soc., 77, 2861 (1955)], thiolutin [Angew. Chem., 66, 745 (1954)], aureothricin [J. Am. Chem. Soc., 74, 6304 (1952)], and others. These antibiotics are typically produced by actinomycetes, and are characterized by a sulfur-containing chromophore. Xenorhabdins I–V are substances related to holomycin, and have also been isolated from bacteria (disclosed in WO 84/01775).

Various studies on derivatives of these two groups have been performed, but we are not aware of any disclosure of a substance having the molecular structure of thiomarinol, or which is characterized by its properties.

The third group of compounds is disclosed in publications such as Japanese Application Kokai Numbers 52-102279, 54-12375, 54-90179, 54-103871 and 54-125672, which disclose pseudomonic acid derivatives having a similar structure to thiomarinol, but wherein the terminal carboxylic acid is replaced by an amide group. These compounds do not exert comparable antibacterial activity and do not exhibit a broad spectrum of antibacterial activity. In fact, these compounds demonstrate a tendency to possess weaker antibiotic activity than that of the original pseudomonic acid.

BRIEF SUMMARY OF THE INVENTION

None of the compounds described above has been isolated from Alteromonas spp., and none is identical to thiomarinol. For example, one of the structural features of thiomarinol is the presence of an OH group located between the 6-membered ring and the $\alpha,\beta$-unsaturated carbonyl group. Accordingly, thiomarinol is clearly distinguished from the art.

It is an object of the invention to provide a new compound having improved efficacy and a broader spectrum of antibacterial activity compared with the groups of antibiotics described above.

Thus, the present invention provides a compound of the formula (I):

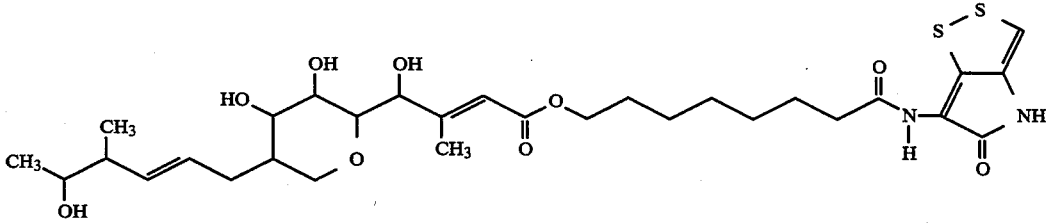

The invention also provides a process for preparing thiomarinol, which comprises cultivating a thiomarinol-producing microorganism of the genus Alteromonas and isolating thiomarinol from the culture.

The invention also provides a pharmaceutical composition comprising thiomarinol in admixture with a pharmaceutically acceptable carrier or diluent.

The invention still further provides the use of thiomarinol in therapy, in particular for the treatment or prophylaxis of bacterial infections.

The invention still further provides the use of thiomarinol for the manufacture of a medicament for the treatment or prophylaxis of bacterial infections.

The invention still further provides a method for the treatment or prophylaxis of bacterial infections, which method comprises administering an effective amount of thiomarinol to a mammal, which may be human, suffering from or susceptible to such an infection.

DETAILED DESCRIPTION OF THE INVENTION

It is clear from the above formula that thiomarinol contains a number of asymmetric carbon atoms and several double bonds. Isomerization is particularly possible at the $\alpha,\beta$-unsaturated carbonyl moiety of thiomarinol. Thiomarinol can, therefore, form various optical and geometric isomers. Although these are all represented herein by a single molecular formula, the present invention includes both the individual, isolated isomers and mixtures thereof, including racemates. Where stereospecific synthesis techniques are employed, or optically active compounds are employed as starting materials, individual isomers may be prepared directly; on the other hand, if a mixture of isomers is prepared, the individual isomers may be obtained by conventional resolution techniques.

Naturally occurring thiomarinol will tend to adopt a standard optical configuration. Thus, while other configurations are provided, the natural configuration is preferred.

Thiomarinol may be prepared by culturing a thiomarinol-producing microorganism of the genus Alteromonas, and then collecting thiomarinol from the culture medium. Variants of thiomarinol possessing the required antibacterial activity may be obtained in a similar manner from other strains or species of Alteromonas which produce the required compound, or they may be obtained by suitable modification of a compound obtained by fermentation as described, or they may be directly chemically synthesised.

In particular, we especially prefer to employ as the microorganism the new species *Alteromonas rava* and particularly the newly isolated strain of *Alteromonas rava* which we have given the strain designation SANK 73390. Strain SANK 73390 is a marine microorganism which was isolated from seawater collected at the seaside of Koina, Minami-Izu Machi, Shizuoka Prefecture, Japan, and this strain has been deposited with the Deposition Institute, Research Institute of Microbiological Technology, Agency of Industrial Science & Technology, Japan, on 30th Apr. 1991, with the Accession no. FERM BP-3381, under the terms of the Budapest Treaty.

The taxonomical characteristics of *Alteromonas rava* strain SANK 73390 are shown below.

1. Morphological characteristics

*Alteromonas rava* strain SANK 73390 was cultured at 23° C. for 24 hours on Marine Agar (Difco). Subsequent microscopic observation revealed that the cells were rod-like in shape and each was 0.8 to 1.0 $\mu$m in diameter and 2.0 to 3.6 $\mu$m in length. This strain is gram-negative, and moves by means of a polar monotricous flagellum.

2. Growth on Marine Agar

SANK 73390 was cultured for 24 hours at 23° C. on Marine Agar (Difco). The resulting colonies were observed to be pale grayish yellow in color, opaque, circular, flat and entire. Water-soluble pigment was not formed.

3. Physiological properties
(1) Seawater requirement: SANK 73390 requires seawater for growth.
(2) Oxidative-fermentative test (Hugh-Leifson method [J. Bact., 66, 24-26 (1953)], in a medium prepared from artificial seawater): no action on carbohydrate.
(3) Oxidase: +
(4) Catalase: +
(5) Oxygen requirement: aerobic
(6) Reduction of nitrate: −
(7) Hydrolysis of starch: +
(8) Decomposition of agar: −
(9) Liquefaction of gelatin: +
(10) DNase production: +
(11) Lipase production: +
(12) Temperature for growth: Poor growth at 4° C., good growth between 17° C. and 26° C., no growth at 35° C.
(13) Growth factor requirement: On the basal medium described in Journal of Bacteriology 107, 268-294 (1971), SANK 73390 requires vitamin-free Casamino Acid.
(14) Assimilation of carbon sources: On the basal medium described in the Journal of Bacteriology 107, 268-294 (1971), additionally comprising 0.1% w/v vitamin-free Casamino Acid, in shaking culture:

TABLE

| | | | |
|---|---|---|---|
| L-Arabinose: | − | D-Ribose: | − |
| D-Xylose: | − | D-Glucose: | + |
| D-Galactose: | − | D-Fructose: | − |
| Maltose: | + | Sucrose: | − |
| Trehalose: | + | Cellobiose: | − |
| Melibiose: | − | Mannitol: | − |
| Sorbitol: | − | Glycerin: | − |
| Sodium acetate: | + | Sodium propionate: | + |

4. Chemotaxonomic character
(1) Mol % of guanine and cytosine (G+C content) of DNA: 43.4% (HPLC method)
(2) Quinone system: Ubiquinone Q-8

Taking into account the taxonomical characteristics shown above, *Alteromonas rava* strain SANK 73390 was compared with the strains described in Bergey's Manual of Systematic Bacteriology, Vol. 1 (1984), as well as with those strains described in recent issues of the International Journal of Systematic Bacteriology. We found that *Alteromonas rava* strain SANK 73390 shared certain similarities with *Alteromonas citrea*, another marine microorganism. SANK 73390 and *Alteromonas citrea*, ATCC 29719 (a standard strain), were comparatively cultured, and compared.

Compared to the pale grayish yellow color of SANK 73390, the colonies of ATCC 29719 were greenish yellow in color. SANK 73390 also differed from *Alteromonas citrea* in growth at 4° C., and in the ability to utilize trehalose and sodium propionate as carbon sources. Accordingly, *Alteromonas rava* strain SANK 73390 is a new strain of the new species *Alteromonas rava*, and differs in essential characteristics from the nearest known species deposited with Accession No. ATCC 29719.

The above-described characteristics are typical of SANK 73390. However, it is well known that the characteristics of Alteromonas spp. are changeable, both naturally and artificially. The characteristics defined above define the strain of *Alteromonas rava* as deposited, but are not necessarily typical of other species of Alteromonas, or of strains of *Alteromonas rava*, which are capable of producing thiomarinol or a naturally occurring variant thereof. Such other strains are included within the scope of the invention.

It will be appreciated that SANK 73390, or any other strain capable of producing a thiomarinol or one of its variants, may be sub-cultured or biotechnologically altered or modified to produce an organism with different characteristics. The only requirement is that the resulting organism be capable of producing the required compound.

Such alterations and modifications may take any desired form, or may be consequent on such considerations as culture conditions, for example. Strains may be modified by culture and so selected as to exhibit such characteristics as enhanced growth, or growth at lower/higher temperatures.

Biotechnological modifications will generally be intentional, and may introduce selectable characteristics, such as bacteriostat resistance or susceptibility, or combinations thereof, in order to maintain purity, or to allow purification of cultures, especially seed cultures, from time to time.

Other characteristics which may be introduced by genetic manipulation are any that are permissible in Alteromonas spp. For example, plasmids encoding resistances may be incorporated, or any naturally occurring plasmids may be removed. Advantageous plasmids include those that confer auxotrophy. Plasmids may be obtained from any suitable source, or may be engineered by isolating a naturally occurring Alteromonas plasmid and inserting a desired gene or genes from another source. Natural plasmids may also be modified in any other manner that may be considered desirable.

In order to obtain thiomarinol from a culture of a suitable microorganism, the microorganisms should be fermented in a suitable medium. Such media are generally well known in the art, and will frequently be used in the production of other fermentation products.

Typically, it will be necessary for the medium to comprise any combination of a carbon source, a nitrogen source and one or more inorganic salts assimilable by the relevant microorganism. The minimum requirement for the medium will be that it contains those ingredients essential for the growth of the microorganism.

Suitable carbon sources include glucose, fructose, maltose, sucrose, mannitol, glycerol, dextrin, oatmeal, rye, corn starch, potato, corn powder, soybean powder, cotton seed oil, syrup, citric acid and tartaric acid, any of which may be employed alone or in combination with one or more others. Typical amounts will be in a range from about 1 to 10% w/v of the amount of medium, although the amount may be varied as desired and in accordance with the desired result.

Suitable nitrogen sources include any substance containing a protein, for example. Representative examples of nitrogen sources are organic nitrogen sources from animals and plants, and may be extracts from such natural sources as soybean powder, bran, peanut powder, cotton seed powder, casein hydrolysate, fermamine, fish powder, corn steep liquor, peptone, meat extract, yeast, yeast extract, malt extract; and such inorganic nitrogen sources as sodium nitrate, ammonium nitrate and ammonium sulfate. As with the carbon source, these may be employed alone or in combination. Suitable amounts are typically within a range from about 0.1 to 6% w/v of the amount of medium.

Suitable nutrient inorganic salts are those which provide trace elements as well as the major constituent of the salt. Preferably, salts should provide such ions as sodium, potassium, ammonium, calcium, magnesium, iron, phosphate, sulfate, chloride and carbonate. Such trace metals as cobalt, manganese and strontium, or salts capable of providing such ions as bromide, fluoride, borate or silicate ions, may also be present.

It will be appreciated that *Alteromonas rava* occurs naturally in seawater, so that, in the absence of indications to the contrary, conditions for its culture will ideally correspond to a marine environment. Thus, trace ions found in the sea are advantageously included in any medium used for the culture of Alteromonas.

If the microorganism is fermented as a liquid culture, it is preferred that an antifoam agent, such as a silicone oil or vegetable oil, or other suitable surfactant, is employed.

It is preferred that the pH of the culture medium for *Alteromonas rava* strain SANK 73390, when used for the production of thiomarinol, is maintained in the region of pH 5.0 to pH 8.0, although the only requirement is that the pH should not prevent growth of the microorganism, or adversely irreversibly affect the quality of the final product. It may be preferred to add an excess of an acid or an alkali to stop fermentation.

*Alteromonas rava* strain SANK 73390, in general, grows at temperatures ranging from 4° C. to 32° C., and grows well at from 17° C. to 26° C. Other temperatures not falling within these ranges may be applicable where a strain has been developed which can grow at lower or higher temperatures. For the production of thiomarinol, a preferable temperature is between 20° C. and 26° C.

Thiomarinol is ideally obtained by aerobic culture, and any suitable aerobic culture techniques, such as, for example, solid culture, shaking culture or aeration-agitation culture may be employed.

If the culture is conducted on a small scale, then a shaking culture fermented for several days at from 20° C. to 26° C. is generally preferred.

To start a fermentative culture, a preferred technique employs an initial inoculum prepared in one or two steps, in an Erlenmeyer flask, for example. A carbon source and a nitrogen source may be used in combination for the culture medium. The seed flask is shaken in a thermostatic incubator at 23° C. for 1 to 3 days, or until sufficient growth is observed. The resulting seed culture may then be used to inoculate a second seed culture, or a producing culture. If a second seeding is conducted, this may be performed in a similar manner, and partly used for inoculation to the production medium. The flask into which the seed is inoculated is shaken for 1~3 days, or until maximal production is obtained, at a suitable temperature. When incubation is complete, the contents of the flask may be collected by centrifugation or filtration.

If the culture is performed on a large scale, culture in a suitable aeration-agitation fermenter may be preferable. In this procedure, the nutrient medium can be prepared in a fermenter. After sterilizing at 125° C., the medium is cooled and seeded with an inoculum previously grown on a sterilized medium. The culture is performed at 20° C. to 26° C. with stirring and aeration. This procedure is suitable for obtaining a large amount of the compound.

The amount of thiomarinol produced by the culture with the passage of time can be monitored by high performance liquid chromatography, for example. In general, the amount of thiomarinol produced reaches a maximum after a period of time between 19 hours and 96 hours.

After a suitable period of culture, the thiomarinol may be isolated and purified by any known means. For example, thiomarinol remaining in the culture broth may be obtained by filtering off the solids, for example, using diatomite as a filtration aid, or by centrifugation and subsequent extraction from the supernatant by purification according to the physicochemical properties of thiomarinol. For example, thiomarinol existing in the filtrate or in the supernatant can be extracted with a water-immiscible organic solvent such as ethyl acetate, chloroform, ethylene chloride, methylene chloride or any mixture thereof, under neutral or acidic conditions, and purified.

Alternatively, as an adsorbent, active carbon or an adsorbing resin such as Amberlite XAD-2, XAD-4 (Rohm & Haas) or Diaion HP-10, HP-20, CHP-20, HP-50 (Mitsubishi Kasei Corporation) may be employed. Impurities can be removed after adsorption by passing the liquid containing the thiomarinol through a layer of the adsorbent; or thiomarinol can be purified after adsorption by elution with a suitable eluent, such as aqueous methanol, aqueous acetone or butanol/water.

Intracellular thiomarinol may be purified by extraction with a suitable solvent, such as 50–90% aqueous acetone or aqueous methanol, subsequently removing the organic solvent, followed by extraction as described above for the filtrate or supernatant.

The resulting thiomarinol may be further purified by well known techniques, for example: adsorption column chromatography using a carrier, such as silica gel or magnesium-silica gel, for example that sold under the trade name "Florisil"; partition column chromatography using an adsorbent such as Sephadex LH-20 (a trade name for a product of Pharmacia); or high performance liquid chromatography using a normal phase or reverse phase column. As is well known in the art, these isolation and purification procedures may be carried out alone or in any suitable combination, and, if desired, repeatedly, to isolate and purify the desired final product.

When the compounds of the invention are intended for therapeutic use, they may be administered alone or in a suitable pharmaceutical formulation containing, in addition to the active compound, one or more conventional diluents, carriers, excipients or adjuvants. The nature of the formulation will, of course, depend on the intended route of administration. However, for the oral route, the compound is preferably formulated as powders, granules, tablets, capsules or syrups. For parenteral administration, it is preferably formulated as an injection (which may be intravenous, intramuscular or subcutaneous) or as drops or suppositories.

The preparations can be prepared by known means by adding such additives as vehicles, binders, disintegrators, lubricants, stabilizers, corrigents, solubilizing agents, suspending agents or coating agents. Although the dosage may vary depending upon the symptoms and age of the patient, the nature and severity of the infection and the route and manner of administration, in the case of oral administration to an adult human patient, the compounds of the present invention may normally be administered at a daily dose of from 20 mg to 2000 mg. The compounds may be administered in a single dose, or in divided doses, for example two or three times a day.

As thiomarinol exhibits an antibacterial effect against gram-positive and gram-negative bacteria in animals (e.g. human, dog, cat and rabbit), it will frequently be desirable to apply it by topical administration, typically in the form of a cream, ointment or gel. Similar considerations for the constituents and preparation of these administration forms apply as with those above.

The following Examples illustrate the preparation of thiomarinol and its antibacterial activity, but are not to be construed as limiting the present invention in any manner whatsoever.

EXAMPLE 1

Jar fermentation of thiomarinol

A) Culture

*Alteromonas rava* strain SANK 73390 was cultured for 3 days at 22° C. on a slant of Marine Agar (product of Difco). The resulting culture was suspended in 3 ml of artificial seawater. 0.1 ml of the suspension was taken aseptically and inoculated into a 500 ml Erlenmeyer flask containing 100 ml of sterilized medium [37.4 g Marine Broth (product of Difco) in 1 liter of deionised water, pH not adjusted].

The flask was incubated for 24 hours at 23° C. with shaking at 200 rpm (rotation radius of 70 mm), using a rotary shaker. After this time, each of four 30 liter jar fermenters, each containing 15 liters of the sterile medium described above, was inoculated with 15 ml of culture taken aseptically from the Erlenmeyer flask. The jar fermenters were incubated for 23 hours at 23° C., at an aeration rate of 7.5 liters/minute, with stirring (100 rpm).

B) Isolation

After 23 hours, the contents of the fermenters were combined to yield 60 liters of culture liquid. The pH of the liquid was then adjusted to a value of 3 with the addition of hydrochloric acid, followed by the addition of 60 liters of acetone, and the mixture was extracted for 30 minutes, with stirring. Using 1.2 kg of Celite 545 filter aid (Trade Mark of a product obtainable from Johns Manville Co.), the solution was filtered. 110 liters of the resulting filtrate was then extracted once with 60 liters of ethyl acetate, and twice with ethyl acetate, each time with 30 liters. The organic layer was washed with 30 liters of 5% w/v aqueous sodium hydrogencarbonate solution, and subsequently with 30 liters of saturated aqueous sodium chloride solution, dried over anhydrous sodium sulfate, and condensed to dryness by evaporation under reduced pressure to obtain 14 g of an oily substance.

The oily substance obtained was dissolved in methylene chloride and the solution adsorbed on a column packed with 200 g of silica gel in methylene chloride. The target compound was eluted by elevating the polarity of the developing solvent in the order: methylene chloride/ethyl acetate; ethyl acetate; ethyl acetate/methanol. The eluent was collected in fractions of 18 ml, and the fractions eluted with ethyl acetate-methanol which contained thiomarinol were saved.

The saved fractions were condensed to dryness by evaporation to obtain 7 g of an oily substance, which was dissolved in 400 ml of 50% by volume of aqueous methanol and adsorbed on 600 ml of a column packed with Diaion HP-20 (Trade Mark of a product obtainable from Mitsubishi Kasei Corporation.) in water. After washing with 50% v/v aqueous methanol, the target substance was eluted with 90% v/v aqueous methanol and, after condensation to dryness under reduced pressure, 1 g of a yellow powder was obtained. The yellow powder was further eluted on a column chromatogram using Sephadex LH-20, and developed with methylene chloride:ethyl acetate:methanol (19:19:2 by volume) to collect the active fractions. 750 mg of thiomarinol was obtained as a yellow powder.

The resulting thiomarinol had the properties shown below.

1) Nature and appearance: Yellow powder.

2) Melting point: 84°–89° C.

3) Molecular formula: $C_{30}H_{44}N_2O_9S_2$.

4) Molecular weight: 640, determined by FAB-MS method ("FAB-MS" is East Atom Bombardment Mass Spectrometry).

5) High resolution mass spectrum: $C_{30}H_{45}N_2O_9S_2$ [(M+H)+ by FAB-MS method]: Calculated: 641.2567 Found: 641.2585.

6) Elemental analysis: Calculated: C, 56.23%; H, 6.92%; N, 4.37%; S, 10.01% Found: C, 55.92%; H, 6.82%; N, 4.23%; S, 9.90%

7) Infrared absorption spectrum: the infrared spectrum showed the following absorption maxima (KBr disc method, $\lambda_{max}$ cm$^{-1}$): 3394, 2930, 1649, 1598, 1526, 1288, 1216, 1154, 1102, 1052.

8) Ultraviolet absorption spectrum: In methanol, or methanol+HCl, thiomarinaol has the ulraviolet absorption spectrum shown below: [given as $\lambda_{max}$ nm ($\epsilon$)] 387 (12,000), 300 (3,500), 214 (26,000) and in methanol+NaOH has the ultraviolet spectrum shown below: [given as $\lambda_{max}$ nm ($\epsilon$)] 386 (9,600), 306 (3,200), 206 (25,000).

9) Specific rotation: $[\alpha]_D^{25} = +4.3°$ (C=1.0, methanol).

10) High performance liquid chromatography:
Separating column: Senshu-Pak ODS H-2151 (Column size, 6×150 mm, Product of Senshu Scientific Co., Ltd.)
Solvent: 40% v/v aqueous acetonitrile
Flow rate: 1.5 ml/minute
Wave length: 220–350 nm (detected by photodiode array)
Retention time: 5.9 minutes.

11) $^1$H-Nuclear magnetic resonance spectrum: ($\delta$ ppm) the Nuclear magnetic resonance spectrum (270 MHz) hexadeuterated dimethyl sulfoxide, using tetramethylsilane as the internal standard, is shown below: 0.91 (3H, doublet, J=6.8 Hz); 0.95 (3H, doublet, J=5.9 Hz); 1.30 (6H, broad multiplet); 1.55 (5H, broad multiplet); 2.03 (3H, singlet); 2.09 (3H, multiplet); 2.34 (2H, triplet, J=7.3 Hz); 3.33 (1H, doublet, J=10.7 Hz); 3.52 (2H, multiplet); 3.64 (2H, multiplet); 3.73 (1H, doublet of doublets); 4.02 (2H, triplet, J=6.6 Hz); 4.18 (1H, broad doublet, J=7.3 Hz); 4.30 (1H, doublet, J=4.4 Hz); 4.44 (1H, doublet, J=7.8 Hz); 4.63 (1H, doublet, J=3.4 Hz); 4.89 (1H, doublet, J=7.3 Hz); 5.37 (2H, multiplet); 5.97 (1H, broad singlet); 7.04 (1H, singlet); 9.80 (1H, broad singlet); 10.68 (1H, broad singlet).

12) $^{13}$C-Nuclear magnetic resonance spectrum: ($\delta$ ppm): the nuclear magnetic resonance spectrum (68 MHz) in tetradeuterated methanol, using tetramethylsilane as the internal standard, is shown below: 174.3 (singlet), 170.4 (singlet), 168.6 (singlet), 161.1 (singlet), 137.9 (singlet), 135.7 (doublet), 135.1 (singlet), 129.8 (doublet), 116.3 (doublet), 115.8 (singlet), 113.7 (doublet), 77.6 (doublet), 74.4 (doublet), 72.1 (doublet), 71.8 (doublet), 66.0 (triplet), 65.7 (doublet), 64.9 (triplet), 45.3 (doublet), 43.9 (doublet), 36.6 (triplet), 33.4 (triplet), 30.1 (triplet), 30.0 (triplet), 29.7 (triplet), 27.0 (triplet), 26.7 (triplet), 20.3 (quartet), 16.6 (quartet), 16.3 (quartet).

13) Solubility: Soluble in an alcohol such as methanol, ethanol, propanol and butanol; and soluble in dimethyl sulfoxide, dimethylformamide, chloroform, ethyl acetate, acetone and ethyl ether; insoluble in hexane and water.

14) Color reactions: Positive to sulfuric acid, iodine and potassium permanganate.

15) Thin layer chromatography:
Rf value: 0.57
Adsorbing agent: Silica gel (Merck & Co. Inc., Art. 5715)
Developing solvent: methylene chloride:methanol=85:15 by volume.

TEST EXAMPLE 1

Antibacterial activity of thiomarinol

The minimum inhibitory concentration (MIC) of thiomarinol, given as μg/ml, against gram-positive and gram-negative bacteria was determined by the agar medium dilution method, using a nutrient agar medium (Product of Eiken Chemical Co., Ltd.).

The results are given in Table 1 below.

TABLE 1

| Test bacterial strain | MIC (μg/ml) |
| --- | --- |
| Staphylococcus aureus 209P | ≦0.01 |
| Staphylococcus aureus 56R | ≦0.01 |
| Staphylococcus aureus 535 (MRSA) | ≦0.01 |
| Enterococcus faecalis 681 | 0.02 |
| Escherichia coli NHIJ | 0.8 |
| Escherichia coli 609 | 0.8 |
| Salmonella enteritidis | 0.4 |
| Klebsiella pneumoniae 806 | 0.8 |
| Klebsiella pneumoniae 846 (R) | 0.2 |
| Enterobacter cloacae 963 | 1.5 |
| Serratia marcescens 1184 | 3.1 |
| Proteus vulgaris 1420 | 0.05 |
| Morganella morganii 1510 | 6.2 |
| Pseudomonas aeruginosa 1001 | 0.2 |
| Pseudomonas aeruginosa N07 | 0.4 |

TEST EXAMPLE 2

Antimycoplasmal Activity of Thiomarinol

Following the procedure as described below, the activity of thiomarinol was assayed against various species of mycoplasma. The results are given in Table 2, below.

TABLE 2

| Strain | MIC (μg/ml) |
| --- | --- |
| Mycoplasma bovis Donetta | 0.0125 |
| Mycoplasma gallisepticum PG-31 | 0.05 |
| Mycoplasma gallisepticum S-6 | 0.10 |
| Mycoplasma gallisepticum K-1 | 0.05 |
| Mycoplasma synoviae WVU1853 | <0.006 |
| Mycoplasma hyosynoviae S-16 | 0.025 |

| | |
| --- | --- |
| Inoculum: | 0.005 ml of $10^5$ CFU/ml |
| Media for assay: | |
| M. bovis and M. gallisepticum | Chanock medium [prepared as described in P.N.A.S., 48, 41–49 (1962) and supplemented with 20% horse serum] |
| M. synoviae | Frey medium [prepared as described in Am. J. Vet. Res., 29, 2163–2171 (1968), and supplemented with 12% swine serum] |
| M. hyosynoviae | Mucin PPLO* agar medium (15% horse serum supplemented) |
| Culture conditions: | 37° C., 5 days, slightly aerobic (BBL gas pack method [cultivation in disposable $CO_2$ generator frpm Becton Dickinson Microbiology Systems, Cockeysville, MD 2103 USA]) |

\* — PPLO (PleuroPneumonia-Like Organism)

| | |
| --- | --- |
| PPLO Broth without CV (Difco) | 21 g |
| Mucin bacteriological (Difco) | 5 g |
| Distilled water | 800 ml |
| Agar Noble (Difco) | 12 g |
| Equine serum | 150 ml |
| 25% Fresh yeast extract | 50 ml |

What is claimed is:

1. A biologically pure culture of *Alteromonas rava* strain SANK 73390, as identified by the Accession no. FERM BP-3381.

2. A process for preparing a compound of the formula

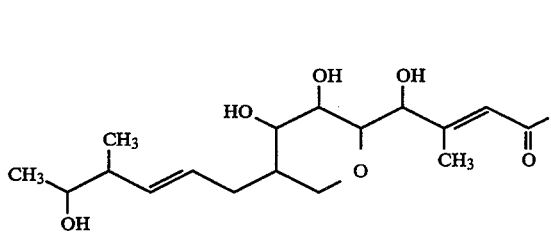

comprising cultivating a culture of a microorganism of the genus Alteromomas which is capable of producing said compound, and isolating said compound from said culture.

3. The process of claim 2, wherein the process is carried out at a pH of 5.0 to 8.0.

4. The process of claim 5, wherein the process is carried out for 19 to 96 hours.

5. The process of claim 2, wherein said microorganism is *Alteromonas rava*.

6. The process of claim 2, wherein said microorganism is *Alteromonas rava* strain SANK 73390, as identified by the Accession no. FERM BP-3381.

* * * * *

UNITED STATES PATENT AND TRADEMARK OFFICE
CERTIFICATE OF CORRECTION

PATENT NO. : 5,405,762

DATED : April 11, 1995

INVENTOR(S) : TAKAHASHI et al

It is certified that error appears in the above-identified patent and that said Letters Patent is hereby corrected as shown below:

```
Column 12, line 3 (claim 4):   replace "claim 5"
          with --claim 3--.
```

Signed and Sealed this

Second Day of December, 1997

Attest:

BRUCE LEHMAN

Attesting Officer

Commissioner of Patents and Trademarks